United States Patent [19]

Moorby et al.

[11] 4,422,320
[45] Dec. 27, 1983

[54] WEDGE TIGHTNESS MEASURING DEVICE

[75] Inventors: Donald G. Moorby; Graham T. McMillen; Ralph S. Flemons, all of Peterborough, Canada

[73] Assignee: Canadian General Electric Company Limited, Toronto, Canada

[21] Appl. No.: 344,795

[22] Filed: Feb. 1, 1982

[30] Foreign Application Priority Data

Feb. 20, 1981 [CA] Canada .................................. 371363

[51] Int. Cl.³ .......................... G01N 3/30; G01M 7/00
[52] U.S. Cl. .......................................... 73/12; 73/572; 73/844
[58] Field of Search ........................... 73/572, 844, 12

[56] References Cited

U.S. PATENT DOCUMENTS 4,030,339  6/1977  Yakshin et al. .......................... 73/12
4,157,655  6/1979  Campbell et al. ....................... 73/12

FOREIGN PATENT DOCUMENTS 44093  1/1982  European Pat. Off. ................ 73/12

*Primary Examiner*—Howard A. Birmiel
*Attorney, Agent, or Firm*—Raymond A. Eckersley

[57] ABSTRACT

A device for determining the tightness of a wedge used to close the slot of a dynamoelectric machine and firmly restrain the conductors installed in the slot, is in the form of a tapping hammer or similar tapping tool. The head of the hammer contains an accelerometer which outputs a pulse signal having a duration representing the time the head is in contact with the wedge. The pulse signal duration is also related to the tightness of the wedge. Associated electronic circuitry measures the time duration and displays the measured value on a digital display on the hammer unless this display is inhibited. The strength of each blow is assessed by an integrating circuit which gives an output related to the strength of the blow. If this output is not within predetermined upper and lower limits, defining a "window", the display of the measured time duration is inhibited and instead the display indicates that the blow was too hard or too weak. The operator quickly learns to strike a wedge with a force that is within acceptable limits, i.e., within the "window". The display is reset each time a new blow is struck. The device is battery powered and portable and preferably the display shuts off if there is an inactive time duration, say 30 seconds, after one blow is struck.

8 Claims, 7 Drawing Figures

WEDGE TIGHTNESS MEASURING DEVICE

BACKGROUND OF THE INVENTION

This invention relates to a device for determining the tightness of wedges in a dynamoelectric machine.

In larger dynamoelectric machines there are slots formed in a laminated stack of iron sheet material to receive the winding conductors. The conductors are installed in these slots and they must be held firmly in place against mechanical and electromagnetic forces which tend to cause movement. The slots are usually formed with a dove-tail adjacent the slot mouth or slot opening for receiving a key or wedge of mating configuration to the dove-tail. Many forms of wedges have been developed and many materials used for the wedges. One common form of wedge configuration is a two part assembly where an outer part fits into the dove-tail and closes the slot opening and an inner part in the form of a shim or "wedge" is tapped or driven into position engaging both the outer part and the conductors (i.e., the packing material or filler usually placed over the conductors) to exert a force between them and prevent movement of the conductors. The wedge assemblies, or more simply wedges, are normally installed by a skilled workman who has developed the ability to install the wedge to a required tightness, i.e., with a desired force restraining the conductors. The workman may test the tightness by lightly tapping the installed wedge with a hammer or similar device and listening for the "ring". The resulting ring varies with the tightness and the workman is able to install the wedges to a desired tightness in this manner.

It will be apparent that this form of testing for the tightness of a wedge requires considerable individual skill that is not easily acquired. There are a limited number of workmen with this skill who may be normally available at a manufacturing facility but are often not readily available for testing and repair at an installed dynamoelectric machine. In addition, this method of testing for wedge tightness does not lend itself to precise control of production.

In recent years there have been attempts to reduce the testing of wedges for tightness to a more exact science. One such attempt measured the initial deflection of an installed wedge body and then monitored the deflection. A decrease in deflection indicated a change in the degree of tightness. This procedure for determining wedge tightness may be quite precise, but it is very time consuming and not practical in commercial production. In addition, it relies heavily on the accuracy of very small initial and subsequent measurements.

The present invention provides a means for a technician who is not skilled in the installation of wedges to determine wedge tightness quickly and to a desired commercial accuracy, not only during manufacture but subsequently.

It should be pointed out here that it is important not only to determine wedge tightness when the wedges are initially installed, but also to determine wedge tightness in a dynamoelectric machine that has been in service for some time and is, for example, having routine maintenance or inspection performed.

Conductors in larger dynamoelectric machines usually have a jacket formed of a thermosetting resinous material impregnating a porous material and that is cured to a hard state forming the insulating jacket around the conductor. In addition, there may be portions of the jacket coated with a partially conducting elastomer to provide intimate contact with the slot walls and maintain a conductive path to ground. When these conductors are first installed they are very firmly wedged into their slots and are satisfactorily restrained against movement in a radial direction. However, with time the possibility of decreasing restraining forces, with a decrease in wedge tightness, has been a problem. Repeated thermal cycling may possibly permit some compression set of the slot contents or there may be some shrinkage. The conductors may carry quite large currents and the electromagnetic forces may be correspondingly large. This, perhaps in conjunction with compression set, may eventually result in a decrease in the restraining forces which can be detected by determining that a decrease in wedge tightness has occurred. It is therefore important to be able to determine wedge tightness in the field, that is at a particular installation of a dynamoelectric machine, when the machine is shut down for maintenance or overhaul.

The present invention provides a device that can be used with a minimum of training to measure or determine if wedge tightness is within required limits.

SUMMARY OF THE INVENTION

It is an object of the invention to provide a device for determining if the tightness of wedges in a dynamoelectric machine are within predetermined limits.

It is another object of the invention to provide a device that can be used with a minimum of training for determining wedge tightness.

It is an object of the invention to provide a device which enables different individuals to obtain substantially uniform results when testing for tightness of wedges.

It is a further object of the invention to provide a portable device for obtaining a readout or indication showing the degree of tightness of a wedge in a dynamoelectric machine.

Very briefly, the present invention is in the form of a small tapping cylinder or tapping hammer. For convenience, the tapping unit may be referred to as a hammer whether or not it has a handle protruding from the side of the tapping cylinder or head. The head contains a accelerometer at the tapping end and a digital or other display which is conveniently at the rear of the head. The display gives an indication of tightness when the wedge is tapped with a blow whose strength falls within predetermined limits. The circuitry associated with the device is normally connected by cable to the head. A battery powered supply is used to make the device portable.

Accordingly, there is provided a device for determining the tightness of a wedge in a dynamoelectric machine, comprising a tapping unit containing an accelerometer for tapping the wedge, said accelerometer providing a pulse having a time duration representing the time interval said tapping unit is in contact with said wedge, means deriving a signal proportional to said pulse duration, and display means responsive to said signal for displaying a value proportional to said pulse duration.

PREFERRED EMBODIMENTS OF THE INVENTION

The principle or operation of the device is quite straightforward and will be discussed first. When a hammer strikes a wedge there is a force exerted on the hammer by the wedge and this force is proportional to the deflection of the wedge over a limited range of deflection. The force decelerates the hammer, reducing its velocity to zero, and then accelerates the hammer away from the wedge. The hammer of this invention contains an accelerometer in the head. Before the hammer strikes the wedge it is accelerated towards the wedge by the person holding the hammer. This acceleration lasts over a relatively long time and is quite small. When the hammer strikes the wedge it compresses or deflects the wedge and this produces a relatively strong output signal from the accelerometer. For convenience we can call the output positive. This output signal increases to a maximum as the velocity of the hammer is reduced to zero. The deflected wedge then applies a force to the hammer causing it to rebound. This sustains the positive output signal from the accelerometer, and the signal reduces as the wedge returns to it original position. The signal is therefore back at its reference position when the hammer leaves the wedge. The shape of the pulse may be, very roughly, similar to the positive half of a sine wave cycle, at least for a tight wedge.

The time interval during which the hammer is in contact with the wedge is indicated by the presence of a positive (as assumed) output voltage from the accelerometer. This time interval is determined, at least primarily, by the mass of the hammer and the stiffness or tightness of the wedge. The time interval will also be determined to a lesser degree by the momentum of the hammer as it strikes the wedge; however, the momentum can be maintained within relatively close limits as explained below, and its effect on the time interval minimized.

Figure 1:
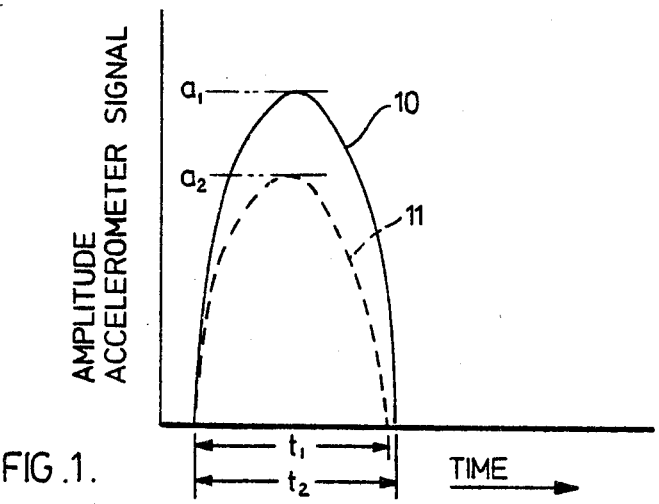
FIGS. 1, 2 and 3 are graphs showing simplified waveforms useful in explaining the invention.

Referring for the moment to FIG. 1, there is shown a graph of the amplitude of the signal of accelerometer output plotted against time for two taps of the same hammer using different momentums for the taps, i.e., for striking a wedge with two different strengths of the blow. The pulse form 10, shown in solid line, is the stronger of the two taps or blows and the pulse form 11 shown in broken line, is the weaker of two taps. Both are shown starting from the same point. It will be seen that the amplitude $a_1$ for waveform 10 is considerably greater than the amplitude $a_2$ for waveform 11. However, the time interval $t_1$ for waveform 11 is only slightly less than the time interval $t_2$ for waveform 10. In other words, when striking the same wedge, a relatively large change in the striking force, i.e., in amplitude, results in a much smaller change in the time interval.

Figure 2:
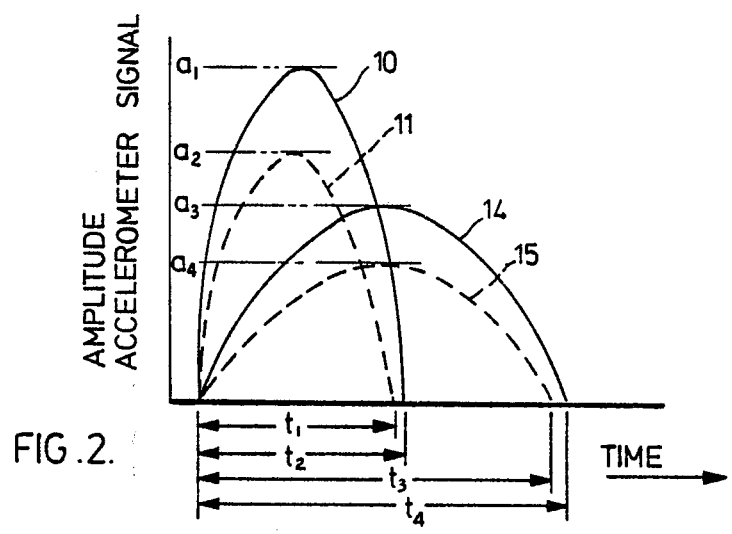

Referring now to FIG. 2, the waveforms 10 and 11 are repeated and two waveforms 14 and 15 are added. The waveforms 10 and 11, previously described, represent the accelerometer pulse signal when striking a tight wedge using two different strengths of blow. When a loose wedge is struck, waveform 14 (shown as a solid line) represents the accelerometer pulse signal as it might appear if the blow were approximately of the same order of strength as produced waveform 10. Similarly, when a loose wedge is struck with a blow of lesser strength, say approximately of the same order of strength as produced waveform 11, the accelerometer pulse signal is represented by waveform 15 (in broken line). It will be seen that the two blows causing waveforms 14 and 15 have amplitudes $a_3$ and $a_4$ respectively and they are considerably different. However, the difference in the strength of blow results in relatively little difference between time interval $t_3$ and $t_4$. It will be seen that the time interval $t_1$ for a tight wedge is quite considerably shorter than the time interval $t_3$ for a loose wedge. Thus, the degree of wedge tightness has far more effect on the time interval than the different strengths of blows used to tap the wedge.

Because the time interval represented by the accelerometer pulse signal is considerably more responsive to wedge tightness than it is to the amplitude, it might be satisfactory to ignore the effect of the strength of the blow. In fact, adequate indication of wedge tightness may be obtained by measuring the time interval of the accelerometer pulse signal and assuming the operator used approximately the same strength of blow each time he tapped a wedge. More satisfactory results could be obtained, however, if only blows with strengths falling within certain predetermined limits were used. It is difficult to distinguish between blows of different strength on the basis, alone, of accelerator signal amplitude because amplitude varies not only with the strength of the blow (amplitude $a_1$ results from a hard blow and $a_2$ from a weaker blow) but also with wedge tightness (amplitude $a_1$ results from a hard blow on a tight wedge and $a_3$ from a hard blow on a loose wedge). It is, however, possible to further evaluate the strength of the blow.

It was discovered that the product of force and time for the blow was directly related to the momentum or strength of the blow. Therefore, integrating the accelerometer signal would give a useful indication of the strength of the blow.

Figure 3:
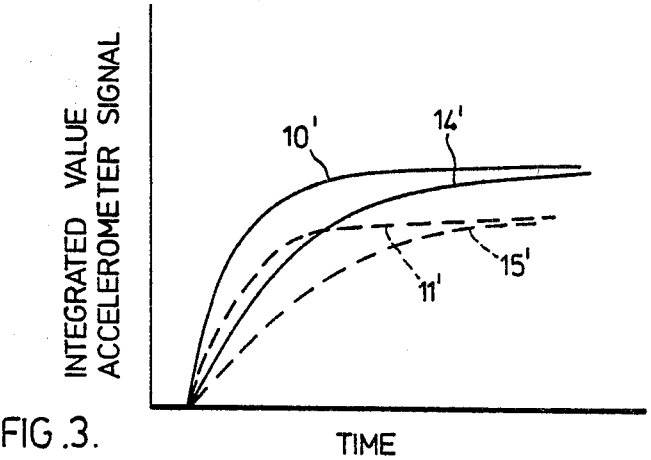

Referring to FIG. 3, there is shown a graph of the integrated accelerometer pulse signals plotted against time. Waveforms 10' and 14' represent strong blows (shown in solid line), and waveforms 11' and 15' represent weaker blows. The results of striking a tight wedge are shown by waveforms 10' and 11' and of striking a looser wedge are shown by waveforms 14' and 15'. It will be seen that when the output from the accelerometer is integrated over a period of time, the stronger blows have a higher value than the weaker blows, regardless of whether the wedge is tight or loose. By setting limits for the integrated signal, the strength of the blow can be controlled. If the integrated signal falls within these predetermined limits, i.e., within the window, the time duration of the accelerometer signal will be used. If the integrated signal is above or below the window, the accelerometer signal will not be used. It will be apparent that by setting these predetermined limits appropriately, the effect of differing strengths of blow on the time interval can be made negligible.

Figure 4:
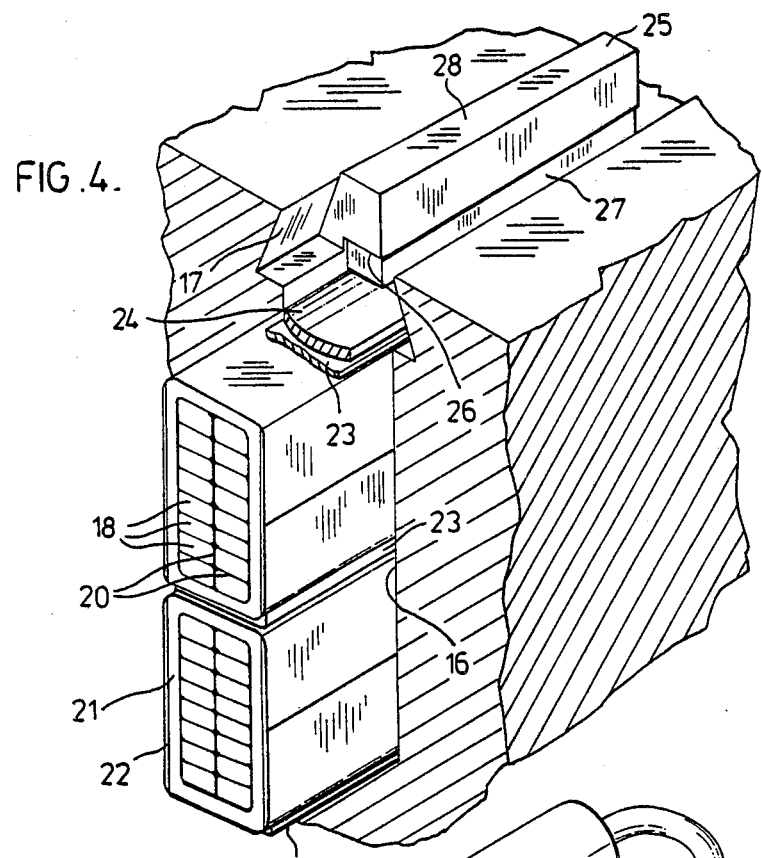
FIG. 4 is a partial sectional view of one form of known wedge shown in a slot of a dynamoelectric machine containing conductors.

Referring now to FIG. 4, an example of one form of two part wedge, is shown in a partial section taken through a slot. FIG. 4 is included only to show one typical form of wedge and forms no part of the invention. Very briefly, a slot 16 is shown having a dove-tail 17 adjacent the slot opening. Conductors 18 are surrounded by insulation 20, and an armour jacket 21 surrounds the group or package of conductors 18. To ensure good contact with the lamination edges forming the slot, an elastomeric material 22 usually is used on the outer surface of the jacket 21. This ensures that no voids develop between the slot edge and the jacket 21. On the conductor package, towards the slot opening, there is a filler strip 23 and a spring 24. The spring is intended to maintain a following force to a predetermined level should a wedge loosen. A two part wedge is shown cut away along its center and has an outer part 25 with a slightly tapered under surface 26. The inner part 27 of the wedge, having a tapered surface for engaging surface 26, is also shown cut away along its center, and engages both the under surface 26 and the spring. During assembly, the inner part 27 is pressed or driven into position, compressing spring 24, until a predetermined tightness is achieved. The tightness may, of course, be tested using the device of the present invention; that is, by tapping the surface 28 of the wedge.

In service, the tightness may decrease, that is, the pressure between the slot conductor package and the wedge may decrease. When the machine is disassembled for maintenance, the tightness can be determined according to the invention and, if necessary, corrective action taken.

Figure 5:
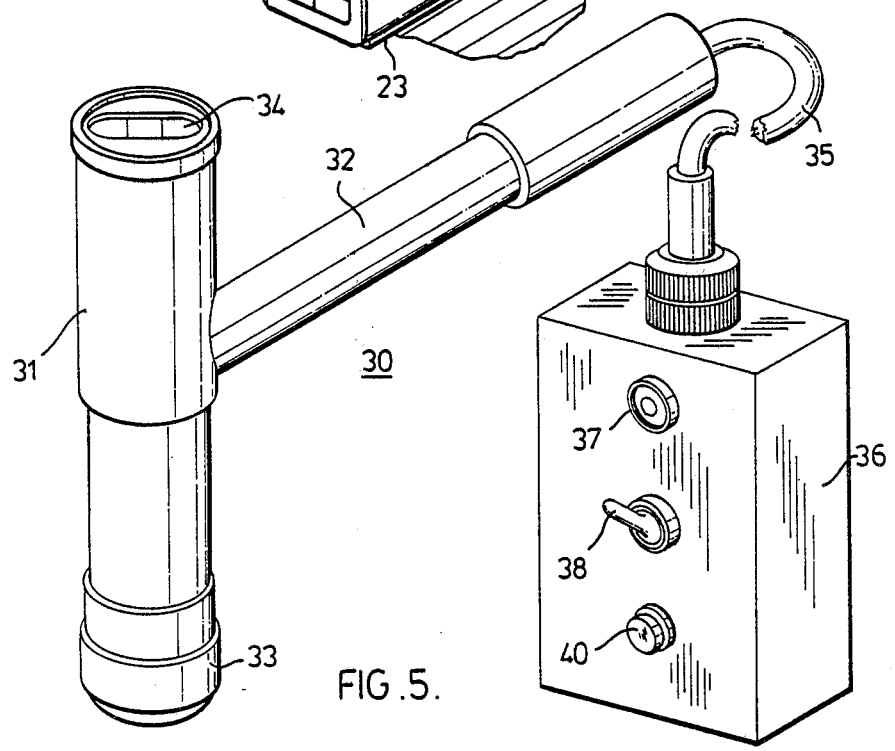
FIG. 5 is an isometric view of the device of the present invention.

Referring now to FIG. 5, a hammer 30 is shown having a head or tapping cylinder 31 and a handle 32. The striking end of the head 31 preferably may have an end piece or cap 33 of hardened steel with a curved striking surface, as shown. The opposite end of head 31 has a digital display 34 having three digits. A cable 35 connects the hammer 30 to an electronic unit 36. The electronic unit 36 contains a rechargeable battery which can be charged from a charging unit (not shown) which connects with female connector 37. The electronic unit 36 includes an on-off switch 38 and a button 40 for recalling the previous display.

Figure 6:
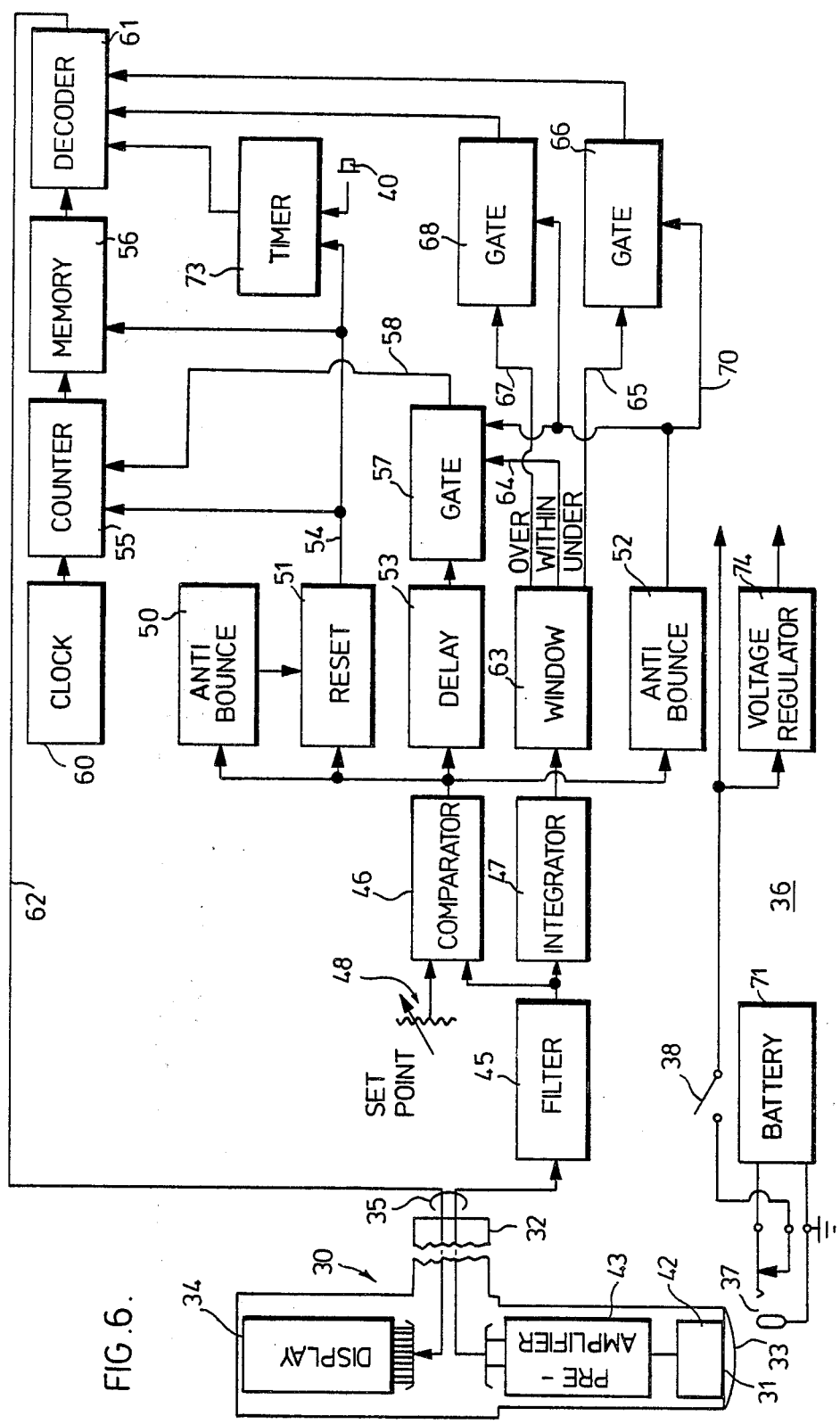
FIG. 6 is a simplified block circuit diagram suitable for the invention.

FIG. 6 is a simplified block schematic diagram where the hammer 30 is shown in outline with head 31 and handle 32. The head 31 has mounted on it, inside the hammer head, an accelerometer 42. The output of accelerometer 42 is coupled to a pre-amplifier 43 which is also mounted in the head 31. A cable 35 extends from the circuitry in the hammer head 31, through the handle 32 to electronic unit 36. All the circuitry and electronic components not shown in the hammer are in the electronic unit 36.

The output from preamplifier 42 is applied to filter 45 via conductors in cable 35. Filter 45 is a low pass filter which removes ringing components from the accelerometer signal. The output from filter 45 is provided at comparator 46 and integrator 47. Comparator 46 compares the signal with a set point or threshold level from control 48 and provides as an output a pulse having a duration corresponding to the time the input was above the set point. The output from comparator 46 is applied to an anti-bounce circuit 50, a reset circuit 51, an anti-bounce circuit 52, and a delay circuit 53. The reset circuit 51 is triggered by the leading edge of the pulse output of comparator 46 to provide a reset signal on conductor 54 which resets a counter 55, a memory 56 and a timer 73. The anti-bounce circuit 50 is conveniently a delay circuit which blocks the reset circuit 51 for a short time, of the order of 0.2 seconds, following the output of a reset signal to prevent immediately subsequent pulses caused by accelerometer bouncing from generating additional reset pulses. Other forms of anti-bounce circuits could be used. However, the delay type circuit is relatively simple and effective and is preferred.

The delay circuit 53 introduces a delay of sufficient length to provide time for the counter 55 and memory 56 to be reset before the active count is received. This delay might be, for example, 15 to 20 microseconds, depending on the resetting time required. The pulse signal output is then applied to gate 57. As will be explained hereinafter, gate 57 is open if the integrated accelerometer output pulse is between an upper and lower predetermined limit, that is, if it falls within a predetermined window. If the accelerometer output pulse is not within this window, gate 57 is closed. If the gate is open or enabled, the pulse signal from the delay circuit 53 is applied to counter 55 via conductor 58. This enables counter 55 for a time period corresponding to the time the pulse output from the accelerometer is above the set point, and the counter counts clock pulses from the clock 60 for that time period. The count obtained is stored in memory 56 and is available via a decoder 61 and conductors 62 to digital display 34 is hammer 30. The count displayed in display 34 is therefore proportional to the duration of the accelerometer pulse output signal and represents tightness as was previously explained.

The integrator 47 receives the pulse signal from filter 45 and provides an integrated signal to an amplitude gate circuit or window circuit 63. As explained previously, the window circuit 63 determines if the pulse falls within two predetermined limits defining a window. If the signal is between these limits, i.e., within the window, an output is provided on conductor 64 to enable gate 57. If the signal is under the window, i.e., does not reach the first predetermined limit, then a signal is provided on conductor 65 to gate 66 which when enabled provides a signal to decoder 61 which, in turn, provides a signal to display 34 (for example a display "U U U") indicating the blow was too weak. If the signal is above the window, i.e., exceeds the second predetermined limit, then a signal is provided on conductor 67 to gate 68 which when enabled provides a signal to decoder 61 which, in turn, provides a signal to display 34 (for example, a display "∩ ∩ ∩") indicating the blow was too strong. The anti-bounce circuit 52 provides a signal on conductor 70 to gates 57, 66 and 68 ensuring they do not respond to pulses immediately subsequent to the striking pulse such as could be caused by accelerator bounce. The anti-bounce circuit 52 is conveniently a delay circuit similar to anti-bounce circuit 50.

The power for the device is preferably provided by a rechargeable battery 71 incorporated into electronic unit 36. A female connector 37 provides a connection for a recharging unit. An on-off switch 38 is provided and a voltage regulator 74 so that both regulated and unregulated voltages are available. The power supply is conventional and this brief description is included only for completeness.

While it is not essential, the electronic circuitry 36 preferably includes a timer 73 which will shut off the display after a predetermined delay, for example 30 seconds, to conserve power. The timer 73 is connected to reset 51 by conductor 54 and its operation is triggered by a reset pulse. After the predetermined period has elapsed, the timer 73 provides an output to deconder 61 turning off the display. The recall button 40 may be operated to re-energize the display with the last value stored in memory.

It will be apparent that the number displayed on display 34 has no tightness unit associated with it. It represents a time duration (the number of counts displayed multiplied by the time period of the internal clock 60 is a time duration). If the time period of the clock 60 is, for example, 4 microseconds, then a display of 342 would represent a time duration of 1368 microseconds.

The devices are calibrated against a reference prior to using. A number for satisfactory wedge tightness on initial assembly is determined, and all wedges are installed to display the determined number using the hammer 30 as described plus or minus a tolerance. Subsequently, when the dynamoelectric machine is shut down for maintenance, a calibrated hammer device 30 can be used to tap the wedges and determined if they have maintained the same tightness, i.e., if the same number is displayed plus or minus the tolerance. If the number is outside the tolerance range (a larger number indicates a looser wedge) then the amount by which it is outside the tolerances will give an indication of how loose it has become. The wedges can be retightened or replaced as required.

It is believed that a complete description of the invention has been provided and that various known circuits could be used to give the functions indicated in FIG. 5. However the circuit diagram has been included as FIG. 7 to ensure the description is complete.

Figure 7:
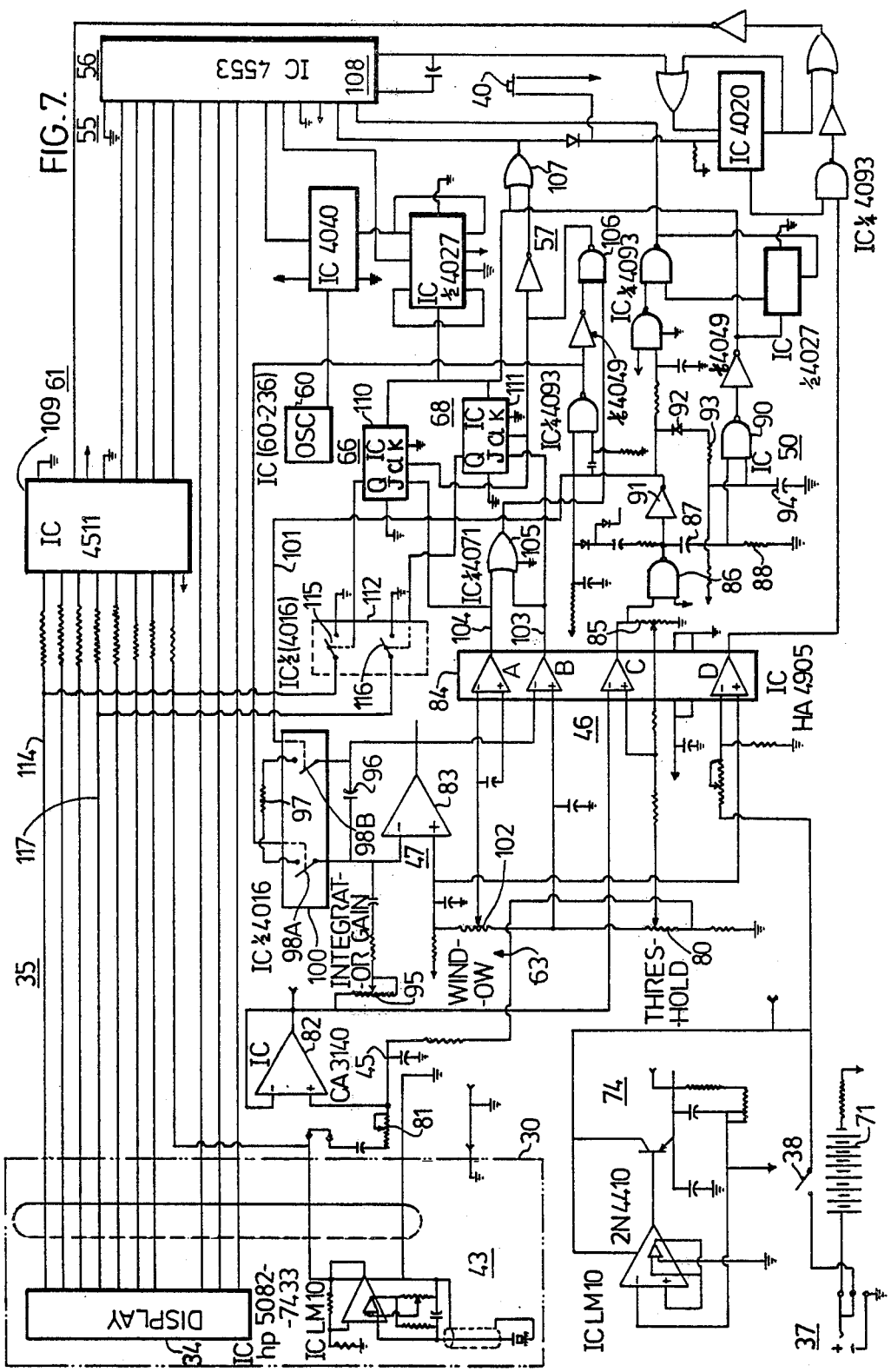
FIG. 7 is a schematic diagram of one form of the invention.

Referring to FIG. 7, which represents one specific form of circuitry suitable to the invention, the integrated circuitry is identified and portions of the FIG. 7 circuitry have a designation number corresponding generally to the block in the FIG. 6 diagram. In FIG. 7, the hammer 30 is represented by a broken line. The hammer 30 incorporates display 34 and preamplifier 43. A cable 35 is shown connecting the hammer circuitry to the remainder of the circuitry.

The signal from the preamplifier 43 is coupled to filter 45. Filter 45 is a low pass filter which includes a variable resistor 81. The resistor 81 provides for adjustment of the cut-off frequency. The filtered signal is applied to IC82 which duplicates the signal at low impedance and this output is applied to integrator 47 which includes IC83. The signal is also applied to comparator 46 which includes IC84C.

There are two controls associated with comparator 46. These are the potentiometers 80 and 85 which control threshold and hysteresis. The threshold control 80 sets the level at which timing starts and stops. The control 85 sets the hysteresis which provides a margin of protection against noise and spurious signals.

The output of the comparator 46 is inverted by IC86 and this represents the timing of the bounce. From this signal there is derived a reset signal and lock-out or anti-bounce signals as was described in connection with FIG. 6. The reset pulse is obtained by differentiating the signal with capacitor 87 and resistor 88 and applying it as an input IC90. To provide lock-out or anti-bounce, the IC90 is disabled for perhaps 0.2 seconds by applying the signal from IC91 through diode 92, resistor 93 and capacitor 94 to IC90. Thus, the trailing edge of the timing signal, i.e., the signal representing pulse duration, is used to lock-out or block IC90 for a short time, preventing the circuit from responding to multiple bounces.

The signal from IC82 goes through a variable resistance 95 which is the integrator gain control, and is applied to IC83. An integrating capacitor 96 is normally shunted by resistor 97, except when switches 98A and 98B (IC100) are opened. The switches 98A and 98B are opened by the timing signal from IC91 over conductor 101. Thus, the integrator functions only during that period of time when there is an incoming signal. The integrator output starts at the voltage of its + input and falls. When the near side of the window voltage is reached, the output from comparator IC84A on conductor 104 swings low. The potentiometer 102 sets the range of the window. If the integrator output, as it continues to fall, does not reach the far side of the window voltage, the momentum is within the allowable window and the output on conductor 103 from IC84 remains low. In other words, the momentum is within allowable limits when the level on conductors 103 and 104 is low. This holds the output from IC105 low blocking IC106 and preventing a reset pulse from propagating via IC107 to reset IC108. In the absence of a reset signal, the count stored in IC108 representing the time duration of the pulse is passed to IC109, decoded, and transferred to the display 34. If the hammer blow has insufficient momentum, conductor 104 remains high, and a reset pulse (from IC91) is passed through IC106 to reset IC108. This resets the counter to zero. In addition the reset pulse from IC106 forms a clock signal to flip-flops IC110 and 111. Now the J input to IC111 on conductor 103 is low causing IC111 to ignore the clock pulse. However, the level on conductor 104 is high since the window voltage has not been reached and this causes IC110 to operate switch 115 of IC112 connecting conductor 114 to ground. This causes the display 34 to show by preventing the "a" segment from operating indicating the blow was weak.

If the hammer blow has too much momentum, the reset pulse causes IC108 to reset as before so the counter is zero. As before the reset pulse forms a clock signal that is applied to IC110 and 111. The conductor 103 is now high and the conductor 104 is now now. This causes IC110 to ignore the clock pulse, and causes IC111 to operate switch 116 shorting conductor 117 to ground. This causes the display to show by preventing the "d" segment of the display from operating, indicating the blow was too strong.

It is believed that all the portions of FIG. 7 essential to the invention have been explained and that the circuitry of FIG. 7 (which is provided only as a specific example of suitable circuitry) will be clear to those skilled in the art.

What we claim as new and desire to secure by Letters Patent of the United States of America is:

1. A device for determining the tightness of an object where tightness is related to the spring-like quality of the object, comprising:
a tapping unit for tapping the object whose tightness is to be determined;
an accelerometer mounted to said tapping unit for providing a pulse signal having a time duration representing the time interval said tapping unit is in contact with said object;
means connected to said accelerometer for receiving said pulse and providing an output representing said time duration only when the time integral of said pulse is between a predetermined upper and a lower limit; and, display means for receiving said output and responsive thereto for displaying a value proportional to said time duration and representing tightness.

2. A device for determining the tightness of an object where tightness is related to the spring-like quality of the object, comprising:
a tapping unit for tapping the object whose tightness is to be determined;
an accelerator mounted to said tapping unit for providing a pulse having a time duration representing the time interval said tapping unit is in contact with said object;
first means connected to said accelerometer for receiving said pulse and providing a first signal representing said time duration;
second means connected to said accelerometer for receiving said pulse and deriving a second signal representing the time integral of said pulse;
third means connected with said first and second means for receiving said first and second signals and having an upper and a lower limit, said third means being responsive to said second signal being above said said upper limit and below said lower limit to inhibit passing of said first signal; and,
display means connected to said third means for receiving said first signal and responsive thereto for displaying a value proportional to said time duration and representing tightness.

3. A device for determining the tightness of a wedge in a dynamoelectric machine, comprising:
a hammer having a head with a tapping end;
a display device mounted in said head in the end opposite said tapping end,
an accelerometer mounted to said head for providing an output pulse signal when the tapping end of said head is tapping against a wedge, said pulse having a time duration, said time duration representing the time interval said tapping end is in contact with said wedge;
gate means connected to said accelerometer and having a predetermined upper and lower levels, said gate means providing a first signal when the time integrated value of said output pulse signal is between said upper and lower levels, providing a second signal when said time integrated value of said output pulse signal is below said lower level and providing a third signal when said time integrated value of said output pulse signal is above said upper level;
means responsive to said first signal and said output pulse signal for deriving a fourth signal proportional to said time duration; and,
display means receiving said fourth signal and responsive thereto for providing a display, said display being an indication of wedge tightness.

4. A device as defined in claim 3 in which said display means also receives said second and third signals and is responsive thereto for providing respectively a display indicating insufficient tapping force and a display indicating excessive tapping force.

5. A device as defined in claim 4 and further including an anti-bounce circuit which inhibits said means responsive to said first signal and said output pulse signal for a predetermined time period following said output pulse signal to prevent immediately subsequent pulses caused by accelerator bounce from being processed.

6. A device as defined in claim 4 and further including a reset means responsive to the leading edge of said output pulse for resetting said display means.

7. A device for determining the tightness of a wedge in a dynamoelectric machine, comprising:
a hammer having a head with a tapping end and an end remote from said tapping end;
a digital display device mounted in said remote end;
an accelerometer mounted in said head at said tapping end for providing a first pulse signal when the tapping end is tapped against a wedge, said first pulse signal having a variable time duration related to the time interval said tapping end is in contact with said wedge;
a pre-amplifier in said head to amplify said first pulse;
an electronic unit connected to cable to said hammer and including:
a filter for receiving the amplified first pulse signal from said pre-amplifier for reducing high frequency ringing components therefrom;
a comparator for receiving the filtered first pulse signal from said filter, comparing said signal to a set point and deriving a second pulse signal having a time duration substantially equal to said time interval;
a clock pulse generator;
a counter connected to said clock pulse generator for counting said clock pulses when in an enabled condition;
a first gate having an enabled condition and a closed condition, said first gate receiving a delayed second pulse signal and when enabled providing said delayed second pulse signal to said counter to enable said counter for a time substantially equal to said time interval whereby the count is proportional thereto;
memory means associated with said counter for storing the count providing by said counter, said memory means being connected to said digital display device to display the stored count;
reset means for receiving the filtered first pulse signal from said filter and responsive to the leading edge thereof to reset said counter and memory means prior to the beginning of each count for the respective said first pulse signal;
integrating means for receiving said first pulse signal and providing a time integrated output signal;
gate means for receiving said time integrated output signal and having predetermined first and second spaced limits, and being responsive to said time integrated output signal being within the values defined by said first and second limits to enable said first gate, and being responsive to said time integrated output signal being outside the values defined by said limits on the side of said first limit and one the side of said second limit providing respectively third and fourth signals; and
means responsive to said third and fourth signals respectively providing to said display device a display indicating the tapping strength was too weak and too strong.

8. A device for determining the tightness of a wedge in a dynamoelectric machine, comprising:
a tapping unit for tapping a wedge,
an accelerometer in said tapping unit for providing a pulse having a time duration representing the time interval said tapping unit is in contact with said wedge,
means for deriving from said pulse a signal proportional to said pulse time duration,
gate means connected to said accelerometer for receiving said pulse and having a spaced apart upper and lower limit, limit responsive means connected with said gate means and responsive to the time integral of the pulse amplitude being below said lower limit to provide a low signal and responsive to said time integral being above said upper limit to provide a high signal, said gate means passing said pulse signals from said accelerometer to said means for deriving from said pulse a signal proportional to said pulse time duration, only those pulses having time integrals falling between said upper and lower limits, display means responsive to said pulse signal passed by said gate means for displaying a value proportional to said pulse time duration, and responsive to said low and high signals respectively for providing thereon a display indicating insufficient and excessive tapping strength.

* * * * *